United States Patent [19]
Mihashi et al.

[11] Patent Number: 6,070,981
[45] Date of Patent: Jun. 6, 2000

[54] OPHTHALMOLOGIC CHARACTERISTIC MEASURING APPARATUS

[75] Inventors: Toshifumi Mihashi; Takefumi Hayashi, both of Tokyo, Japan

[73] Assignee: Kabushiki Kaisha Topcon, Tokyo, Japan

[21] Appl. No.: 09/190,831

[22] Filed: Nov. 12, 1998

[30] Foreign Application Priority Data

Nov. 11, 1997 [JP] Japan .................................. 9-327097

[51] Int. Cl.$^7$ ...................................................... A61B 3/10
[52] U.S. Cl. ............................................................ 351/212
[58] Field of Search .................................... 351/211, 212, 351/215, 221, 246, 247, 205, 206; 600/476, 558, 587; 356/376; 606/4, 5

[56] References Cited

U.S. PATENT DOCUMENTS

| | | | |
|---|---|---|---|
| 5,080,477 | 1/1992 | Adachi | 351/212 |
| 5,909,270 | 6/1999 | Moser et al. | 351/212 |
| 5,920,373 | 7/1999 | Bille | 351/212 |

*Primary Examiner*—George Manuel
*Attorney, Agent, or Firm*—Baker Botts L.L.P.

[57] ABSTRACT

Disclosed is an apparatus for precisely measuring optical characteristics of an eye to be examined, particularly an ophthalmologic characteristic measuring apparatus capable of observing a front portion of the eye as well as measuring optical characteristic of an irregular astigmatism component. The apparatus includes a first illuminating optical system, a first receiving optical system, a first converting member, a first light receiving unit, a second illuminating optical system, a second light receiving optical system, a second light receiving unit, and an arithmetic unit. The first illuminating optical system illuminates convergently a portion near the center of curvature of the cornea of an eye to be examined with first illuminating light rays emitted from a first illuminating light source. The first receiving optical system receives the first illuminating light rays reflected back from the cornea of the eye. The first converting member converts the reflected light rays into at least seventeen beams. The first light receiving unit receives a plurality of light beams converted by the first converting member. The second illuminating optical system projects an index having a specific pattern on the cornea of the eye with second illuminating light rays emitted from a second illuminating light source. The second light receiving optical system receives light rays reflected back from the cornea of the eye. The second light receiving unit receives the second illuminating light rays from the second light receiving optical system. The arithmetic unit determines the shape of the cornea near the center of the eye on the basis of an inclination angle of the light rays obtained by the first light receiving unit, and determines the shape of the cornea at the periphery of the eye on the basis of a position of the second light receiving unit, at which position the second light receiving unit receives the second illuminating light rays.

4 Claims, 12 Drawing Sheets

Z ALIGNMENT

OPHTHALMOLOGIC CHARACTERISTIC MEASURING APPARATUS

BACKGROUND OF THE INVENTION

The present invention relates to an ophthalmologic characteristic measuring apparatus for measuring the shape of the cornea of an eye to be examined, and particularly to an ophthalmologic characteristic measuring apparatus capable of measuring the shape of the cornea precisely in a wide range and more precisely in a narrow range including an important center portion of the cornea.

Conventionally known is an apparatus for measuring the shape of the cornea of an eye to be examined by projecting an index to the cornea and determining a position at which the index is focused.

While the present applicant has developed a technique for measuring the shape of the cornea of an eye to be examined using a wavefront sensor and already filed the patent application thereof, such a technique has a problem that a measuring optical system having a very large aperture must be provided to measure the cornea of the eye in a wide range using the wavefront sensor.

In view of the foregoing, the present invention has been made to provide an ophthalmologic characteristic measuring apparatus capable of more precisely measuring the shape of the more important central portion of the cornea of an eye to be examined using a wavefornt sensor; and projecting a plurality of concentric light beams to the peripheral portion of the cornea of the eye, receiving the reflected light rays, and determining the shape of the peripheral portion of the cornea on the basis of the light receiving positions.

SUMMARY OF THE INVENTION

An object of the present invention is to provide an ophthalmologic characteristic measuring apparatus capable of precisely measuring optical characteristics of an eye to be examined, and particularly observing a front portion of the eye as well as measuring optical characteristics of an irregular astigmatism component. To achieve the above object, according to an aspect of the present invention, there is provided an ophthalmologic characteristic measuring apparatus including a first illuminating optical system, a first receiving optical system, a first converting member, a first light receiving unit, a second illuminating optical system, a second light receiving optical system, a second light receiving unit, and an arithmetic unit. The first illuminating optical system illuminates convergently a portion near the center of curvature of the cornea of an eye to be examined with first illuminating light rays emitted from a first illuminating light source. The first receiving optical system receives the first illuminating light rays reflected back from the cornea of the eye. The first converting member converts the reflected light rays into at least seventeen beams. The first light receiving unit receives a plurality of light beams converted by the first converting member. The second illuminating optical system projects an index having a specific pattern on the cornea of the eye with second illuminating light rays emitted from a second illuminating light source. The second light receiving optical system receives light rays reflected back from the cornea of the eye. The second light receiving unit receives the second illuminating light rays from the second light receiving optical system. The arithmetic unit determines the shape of the cornea near the center of the eye on the basis of an inclination angle of the light rays obtained by the first light receiving unit, and determines the shape of the cornea at the periphery of the eye on the basis of a position of the second light receiving unit, at which position the second light receiving unit receives the second illuminating light rays.

DETAILED DESCRIPTION OF THE PREFERRED EMBODIMENTS

First Embodiment

Figure 1:
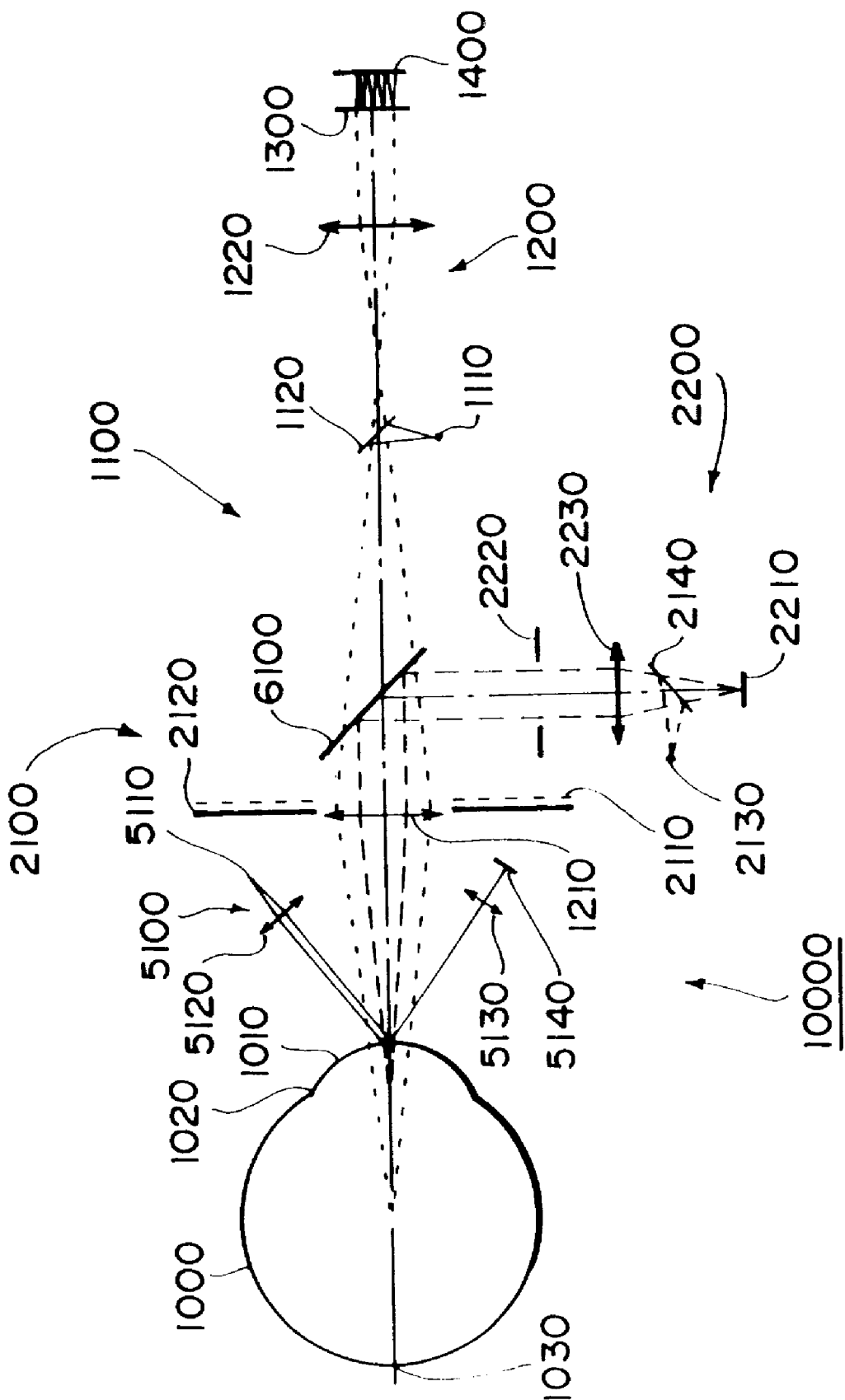
FIG. 1 is a diagram showing the configuration of an ophthalmologic characteristic measuring apparatus according to a first embodiment of the present invention.
Figure 2:
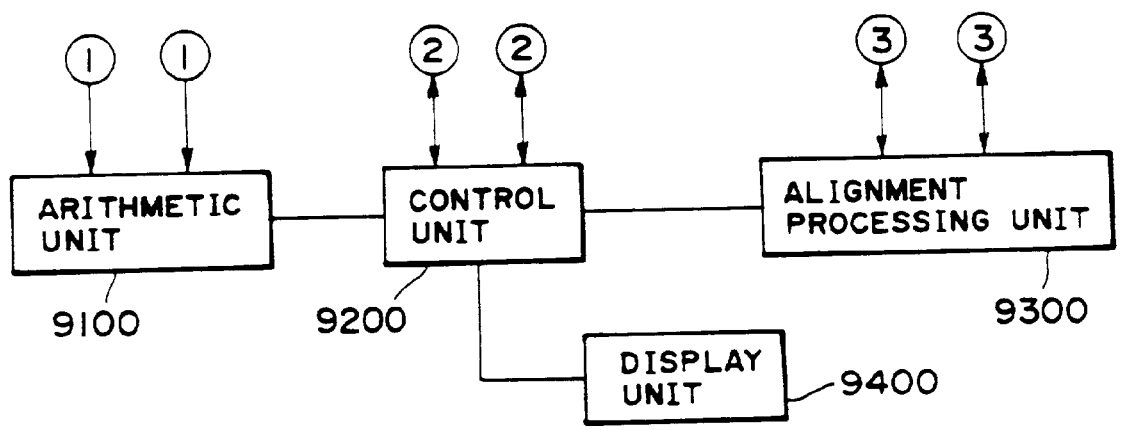
FIG. 2 is a block diagram illustrating the electric configuration of the ophthalmologic characteristic measuring apparatus according to the first embodiment.

As shown in FIGS. 1 and 2, an ophthalmologic characteristic measuring apparatus 10000 according to a first embodiment of the present invention includes a first light source 1110 for emitting light rays having a first wavelength; a first illuminating optical system 1100 for convergently illuminating a portion near the center of curvature of the cornea of an eye to be examined with first illuminating light rays emitted from the first light source 1110; a first light receiving optical system 1200 for receiving the first illuminating light rays reflected from the cornea of the eye and guiding the reflected light rays to a first light receiving unit 1400; a first converting member 1300 for converting the reflected light rays into at least seventeen beams; the first light receiving unit 1400 for receiving a plurality of the light rays converted by the first converting member 1300; a second light source 2110 for emitting light rays having a second wavelength; a second illuminating optical system 2100 for projecting an index having a specific pattern on the cornea of the eye with second illuminating light rays emitted from the second light source 2110; a second light receiving optical system 2200 for receiving the second illuminating light rays reflected from the cornea of the eye and guiding the reflected light rays to a second light receiving unit 2210; the second light receiving unit 2210 for receiving the second illuminating light rays from the second light receiving optical system 2200; and an arithmetic unit 9100 for determining the shape of the cornea near the center of the eye on the basis of an inclination angle of the light rays obtained by the first light receiving unit 1400 and determining the shape of the cornea in the peripheral portion of the eye on the basis of a position of the second light receiving unit 2210 at which position the second light receiving unit 2210 receives the second illuminating light rays.

The first illuminating optical system 1100 convergently illuminates a portion near the center of curvature of the cornea of an eye to be examined with first illuminating light rays emitted from the first light source 1110. To be more specific, the first illuminating optical system 1100 allows the first illuminating light rays emitted from the first light source 1110 to be reflected from a first beam splitter 1120 and then converged to the portion near the center of the curvature of the cornea of the eye.

It may be desirable that the light source 1110 is capable of emitting light having a high spatial coherence and a low temporal coherence. The first light source 1110 of the first embodiment is a superluminescent diode (SLD), which is a point light source having a high luminance.

The first light source 1110 need not be limited to the SLD. For example, a laser which emits light having a high spatial coherence and a high temporal coherence can be employed as the first light source 1110 if a rotary diffuser or the like is inserted in an optical path to lower the temporal coherence properly and appropriately.

A light source material, such as the LED, which is low in both spatial coherence and temporal coherence, can be used if a pinhole or the like is disposed at a position of the light source on the light path, provided that the light source material such as the LED emits a large quantity of light.

The first wavelength of the light emitted from the first light source 1110 of the first embodiment may be set at, for example 780 nm.

An eye 1000 to be examined has the cornea 1010, iris 1020, and retina 1030.

The first light receiving optical system 1200 receives the first illuminating light rays reflected from the cornea 1010 of the eye and guides the reflected light rays to the first receiving unit 1400. The first light receiving optical system 1200 includes an objective lens 1210, a relay lens 1220, and a first converting member 1300 for converting the reflected light rays into at least seventeen beams.

The first light receiving optical system 1200 is preferably configured to be movable in the direction of the optical axis depending on the curvature radius of the cornea of an eye to be examined. This is effective to attain more precise measurement. The first light receiving unit 1400 or the first converting member 1300 is substantially conjugate with the cornea 1010.

As shown in FIG. 2, the arithmetic unit 9100 which is connected to a control unit 9200 calculates optical characteristics or the like on the basis of a command supplied from the control unit 9200. The control unit 9200 controls the entire apparatus including the arithmetic unit 9100. An alignment processing unit 9300 controls alignment processing.

A display unit 9400 displays data outputted from the arithmetic unit 9100. More specifically, the display unit 9400 is capable of displaying arithmetic results of optical characteristics of the eye and the shape of the cornea obtained by the arithmetic unit 9100.

The second illuminating optical system 2100 projects an index having a specific pattern on the cornea 1010 of the eye with light rays emitted from the second light source 2110.

The second light source 2110 emits light having a second wavelength different from the first wavelength of light emitted from the first light source 1110. The second light source 2110 of the first embodiment is set to emit light having a wavelength of 940 nm.

The wavelengths of the first and second light sources may be identical to each other, if light rays emitted from the first and second light sources can be separated through a diaphragm member or the like.

As the second light source 2110 of the first embodiment, an LED is employed.

The second illuminating optical system 2100 includes the second light source 2110 and a Placido's disc 2120.

Figure 3:
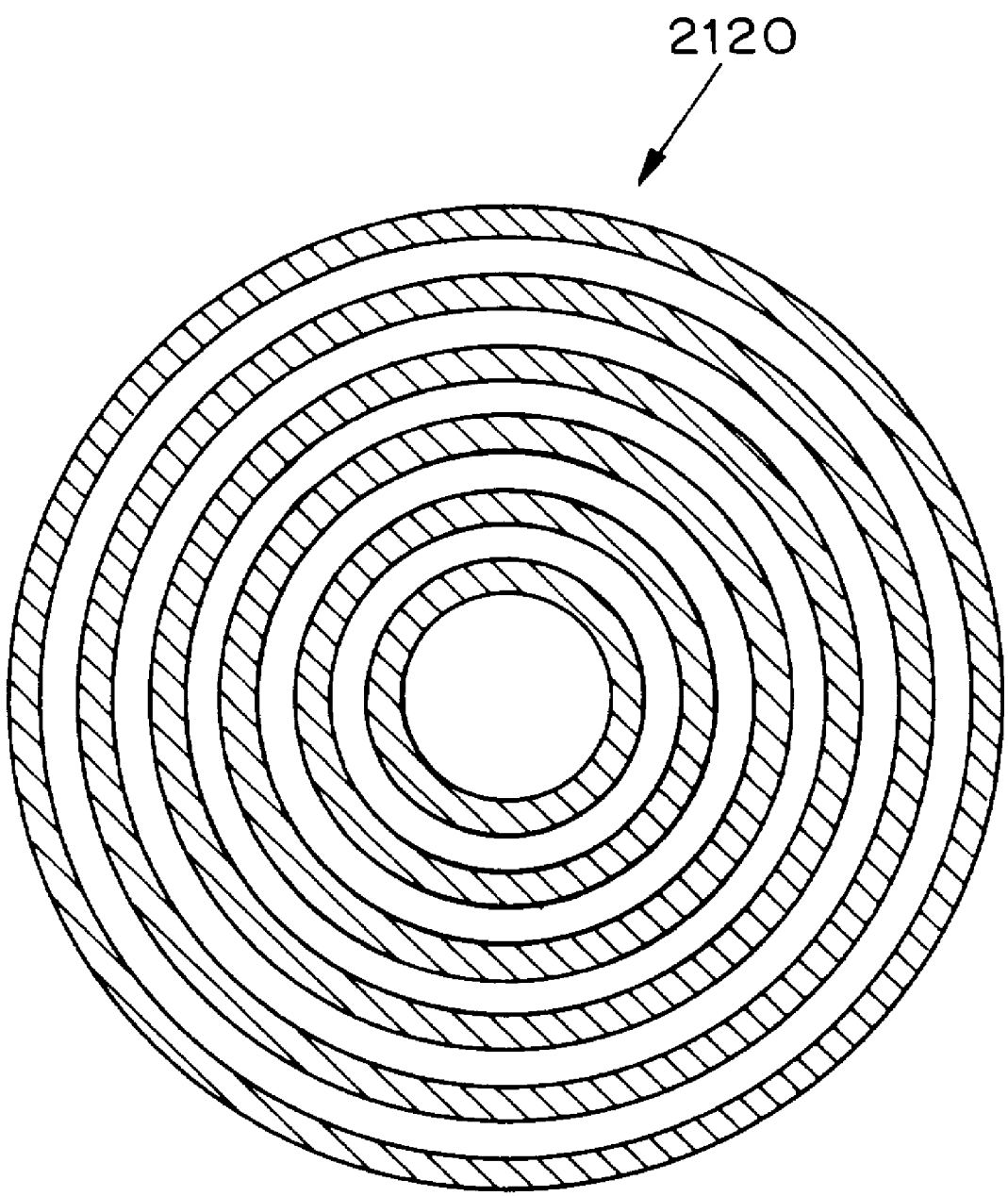
FIG. 3 is a view illustrating a Placido's disc.

As shown in FIG. 3, the Placido's disc 2120 is used for projecting an index having a pattern of a plurality of concentric rings. It should be noted that such an index having a pattern of a plurality of concentric rings is an illustrative example of the index having a specific pattern.

After completion of alignment (which will be described later), the above index having a pattern of a plurality of concentric rings is projected.

The second light receiving optical system 2200 receives the second illuminating light rays reflected from the cornea of the eye and guides the reflected light rays to the second light receiving unit 2210.

The second light receiving optical system 2200 includes an objective lens 1210, a first dichroic mirror 6100, a telecentric diaphragm 2220, and a relay lens 2230.

In the second light receiving optical system 2200 of the first embodiment, the telecentric diaphragm 2220 may be arranged on the focal point on the image formation side from the objective lens 1210 (including the objective lens 1210).

The second light receiving optical system 2200 receives light rays reflected back from the cornea 1010 of the eye to be examined and guides the reflected light rays to the second light receiving unit 2210. At the time of completion of alignment, the second light receiving unit 2210 is substantially conjugate with the cornea 1010.

The second light receiving optical system 2200 also includes an XY alignment function. That is to say, the system 2200 includes the second light source 2130, a relay lens 2230, and the second light receiving unit 2210.

In addition, the second light receiving optical system 2200 of the first embodiment includes an alignment light source 2130 and a second beam splitter 2140.

The second light receiving optical system 2200 projects, after adjustment of alignment, an index of a pattern composed of a plurality of concentric rings to a portion near the cornea 1010 of an eye to be examined.

That is to say, the front eye portion observing system (second illuminating optical system 2200) has the XY alignment optical function and the Placido's observing function.

The Placido's disc having the maximum diameter of 9 mm is accurately projected on the front eye portion. Also, since the second light receiving optical system 2200 is a telecentric optical system having the telecentric diaphragm 2220, if projection of the index is slightly offset in the Z-direction, such offset does not exert any effect on measurement.

However, since a distance between the objective lens 1210 and the vertex of the cornea of the eye must be accurately adjusted, the optical system having a high accuracy is used for alignment in the Z-direction.

The second light receiving unit 2210 of the first embodiment is composed of a two-dimensional CCD, which may be, however, replaced with any one of light receiving devices.

A Z alignment optical system 5100 includes a fourth light source 5110, a collimator lens 5120, a condenser lens 5130, and a linear imaging device 5140.

The converting member 1300 will be described hereinafter.

The converting member 1300 arranged in the light receiving optical system 1400 is a wavefront converting member which converts the reflected light rays into a plurality of light beams. The converting member 1300 has a plurality of micro Fresnel lenses arranged in a plane perpendicular to the optical axis.

The micro Fresnel lens will be described in detail below.

A micro Fresnel lens is an optical element having annular bands at height pitches for wavelengths and an optimized blaze at a focal point. A micro Fresnel lens which can be applied to the present invention has, for example, eight levels of optical path differences produced by semiconductor fine processing techniques, and is capable of achieving focusing at a focusing efficiency of 98% when only primary light is used.

The converting member 1300 of the first embodiment is a wavefront converting member capable Of converting the reflected light rays into at least seventeen light beams.

The Z alignment optical system 5100 is set such that upon adjustment of alignment, light rays which has been emitted from the point light source and reflected from the vicinity of the vertex of the cornea are projected at a specific position (for example, the center) of a linear imaging device 5140.

The linear imaging device 5140 of the first embodiment is a linear PSD, but may be an imaging device of any suitable type.

The Z alignment optical system 5100 collimates light rays emitted from a fourth light source 5110 and illuminates the cornea 1010 with parallel light rays. The linear imaging device 5140 is disposed at a point to receive light rays reflected by regular reflection on a plane including an illumination optical axis and a reflection optical axis.

That is to say, the Z alignment optical system 5100 is disposed so that the parallel light rays approximately coincide with the vertex of the cornea when positioned at a predetermined distance.

Figure 4:
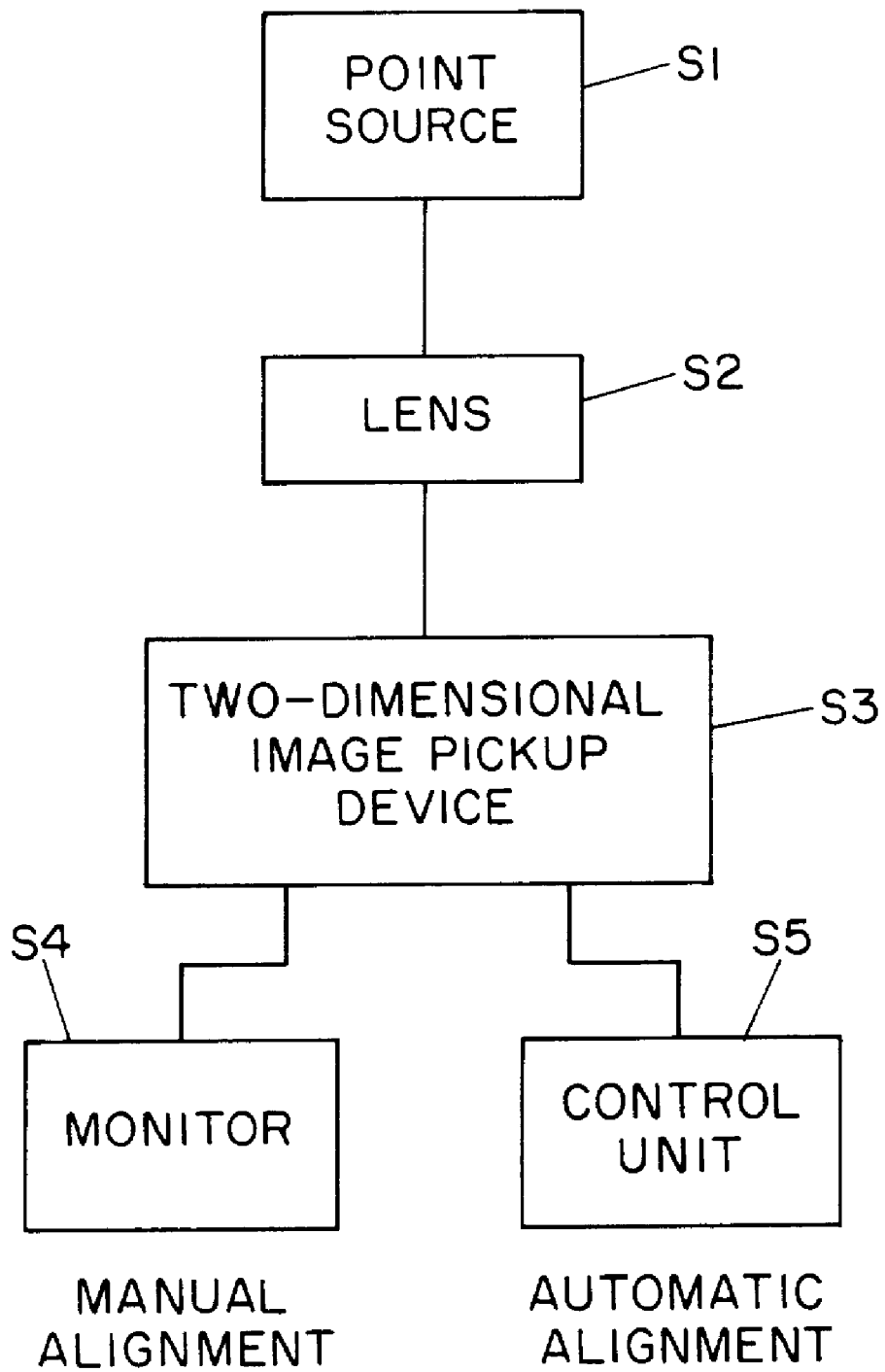
FIG. 4 is a block diagram illustrating XY alignment.

The operation of the XY alignment optical system (second illuminating optical system 2100) will be described with reference to FIG. 4

An alignment light source 2130 is turned on instep S1. The relay lens 2230 and the objective lens 1210 focuses light rays near the cornea 1010 in step S2. The position of a bright point is observed by the second light receiving unit 2210 in step S3. Data is displayed on a monitor in step S4 if manual alignment is selected. Data is sent to the control unit in step S5 if automatic alignment is selected.

Figure 5:
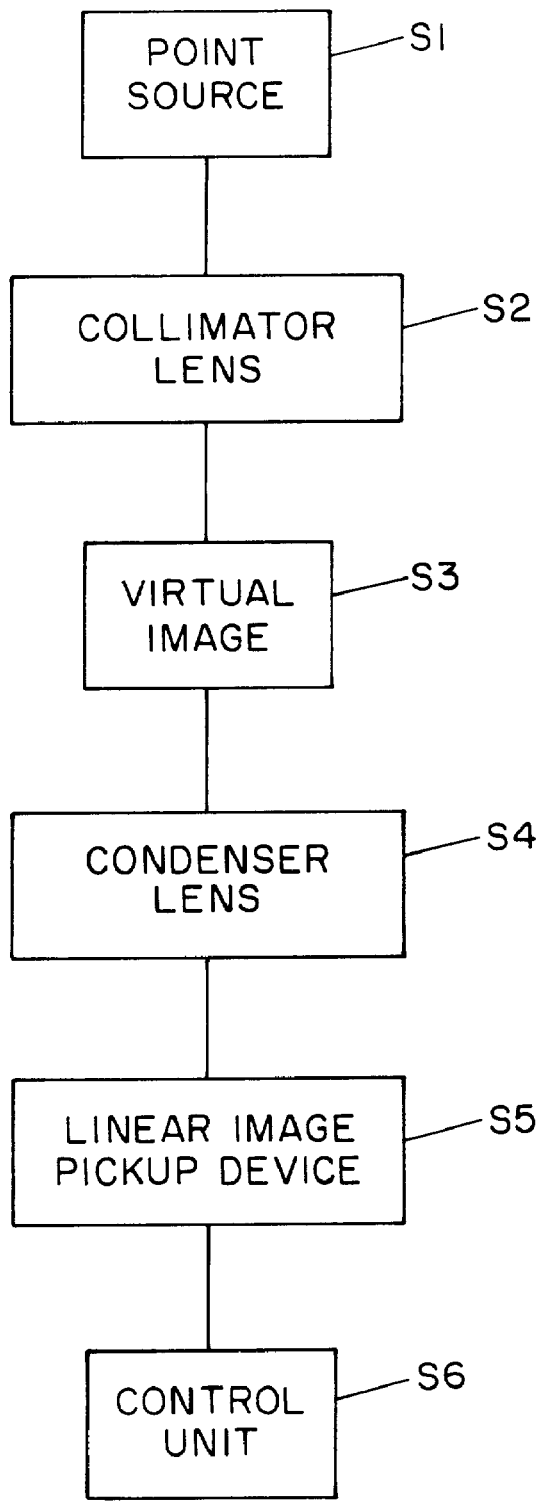
FIG. 5 is a block diagram illustrating Z alignment.

The operation of the Z alignment optical system 5100 will be described with reference to FIG. 5. The fourth light source 5110 is turned on in step S1. Light rays are collimated by the collimator lens 5120 and a portion of the eye 1000 around the vertex of the cornea 1010 is illuminated with parallel light rays in step S2. A virtual image is formed in step S3, and the virtual image is projected on the linear imaging device 5140 by the condenser lens 5130 in step S4. The linear imaging device 5140 provides measured data on the position of the virtual image in step S5 and sends the measured data on the position of the virtual image to the control unit in step S6.

Alignment will be described in detail with reference to FIG. 6 .

Suppose that the lenses on the eye side of the movable lens of the reflected light guiding system form a objective lens group. Alignment can be achieved by disposing the objective lens group so that the front focal point of the objective lens group coincide with a reference measuring plane of a front portion of the eye 1000 (exit pupil, the surface of the cornea).

The movable lens moves so that the front focal point of the movable lens coincides with a point where the measuring light rays traveled through the objective lens group intersect the optical axis. (The point is substantially conjugate with the center of curvature of the cornea 1010 when the shape of the cornea 1010 is measured, and is substantially conjugate with the eyeground when the optical characteristics are measured.) Consequently, substantially parallel light rays fall always on the light receiving device and a measuring region on the reference measuring plane can be substantially fixed.

The accurate position of the light rays on the reference measuring plane of the front portion of the eye 1000 can be determined by measuring the coordinates of the light rays at a point conjugate with the reference measuring plane of the front portion of the eye 1000 after the movable lens on the basis of data on the position at which light rays fall on the light receiving device by interpolation or extrapolation, and dividing the coordinates of the light rays by the lateral magnification of the optical system.

Figure 6:
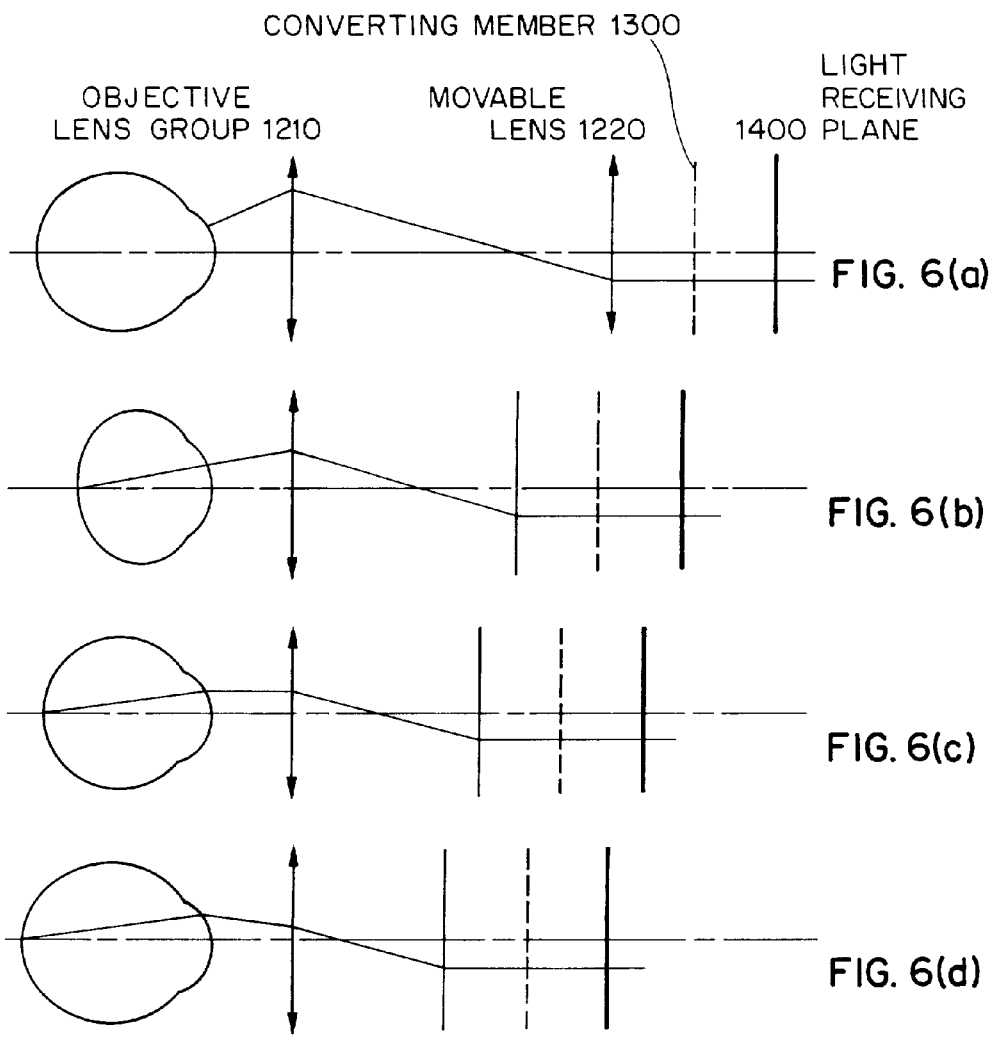
FIG. 6 is a diagram of assistance in explaining alignment.

FIGS. 6(*a*), 6(*b*), 6(*c*) and 6(*d*) illustrates a state for measuring the shape of the cornea 1010, a state for measuring the optical characteristics, a state for measuring emmetropia and a state for measuring myopia, respectively, in which the measuring region on the reference measuring plane is substantially fixed.

The first converting device 1300 will be described.

The first converting device 1300 included in the first reflected light guiding optical system 1200 is a wavefront converting member which converts the reflected light rays into a plurality of light beams. The first converting device 1300 has a plurality of micro Fresnel lenses arranged in a plane perpendicular to the optical axis thereof.

Micro Fresnel lenses will be described in detail.

A micro Fresnel lens is an optical element having annular bands at height pitches for wavelengths and an optimized blaze at a focal point. A micro Fresnel lens which can be applied to the present invention has, for example, eight levels of optical path differences produced by semiconductor fine processing technique, and is capable of achieving focusing at a focusing efficiency of 98% when only primary light is used.

In the first embodiment, the first converting member 1300 is a wavefront converting device capable of converting the reflected light rays into at least seventeen light beams.

The first light receiving device 1100 receives a plurality of light beams from the first converting device 1300. In the first embodiment, the light receiving device 1400 is a CCD. The CCD may be a common CCD for TV use or a CCD having 2000×2000 elements for measurement use.

Although a CCD for TV use as the first light receiving device 1400 has a low resolution, the CCD for TV use is inexpensive and its output can be easily given to a personal computer which is used generally for image processing. NTSC image signals provided by a CCD and its driver can be easily given to a personal computer through an NTSC image input port.

Although a CCD for measurement use having 2000 (2000 elements is expensive, analog signals representing measured values can be given to a personal computer if a CCD for measurement use is employed.

Signals provided by a CCD can be converted into corresponding digital signals, and the digital signals may be given to a personal computer.

The iris 1020 of the eye 1000 is substantially conjugate with the first converting device 1300 or with the first light receiving device 1400.

The first reflected light guiding optical system 1200 maintains the substantially conjugate relation between the first converting device 1300 and the iris 1020 and may be provided with an adjusting system for carrying out adjustment so that the reflected light rays from the eyeground fall in substantially parallel light rays on the light receiving device in a first light receiving state, and the reflected light rays from the cornea 1010 fall in substantially parallel light rays on the light receiving device in a second light receiving state.

The first beam splitter 6100 is inserted in the first reflected light guiding optical system 1200 to direct the light transmitted by the illuminating optical system 1100 toward the eye 1000, and to transmit the reflected light.

The second light receiving device 2400 is the same in configuration and actions as the first light receiving device 1400 and hence the description thereof will be omitted.

The principle of operations of the arithmetic unit 9100 for determining the optical characteristics of the eye 1000 on the basis of the inclination of light rays provided by the first light receiving device 1400 will be described in detail.

An algorithm will be described in detail.

Figure 7:
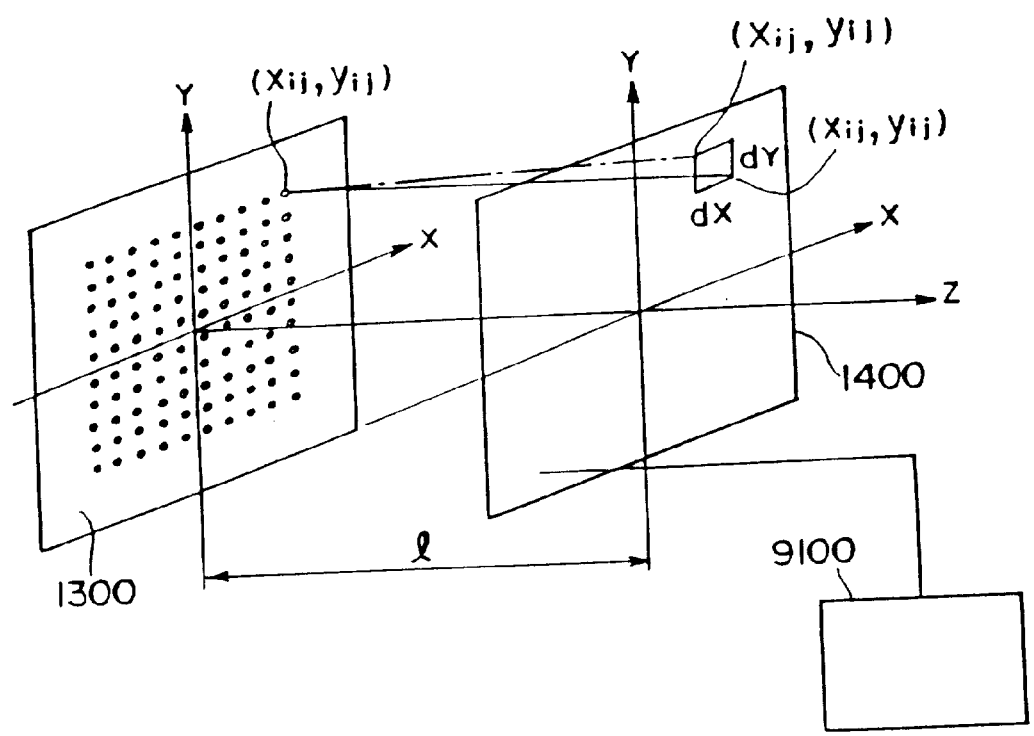
FIG. 7 is a diagram of assistance in explaining the principle of the ophthalmologic characteristic measuring apparatus of FIG. 1.

As shown in FIG. 7, coordinate axes X and Y are set on the first converting device 1300, and coordinate axes x and y are set on the first light receiving device 1400. Then, a wave surface is expressed by a polar coordinate system or a rectangular coordinate system.

$$X = (X'/\beta) \quad (1)$$

$$Y = (Y'/\beta) \quad (2)$$

where $\beta$ is the lateral magnification of the optical system.

If the optical system does not cause aberration, the relation between wavefront aberrations $W(X, Y)$ and $W'(X', Y')$ is expressed by:

$$W\{(X'/\beta),(Y'/\beta)\} = W'(X',Y') \quad (3)$$

The following appropriate polynomial is given.

$f(X, Y, Z \ldots ; A, B, C \ldots)$ where $X, Y, Z, \ldots$ are quantities determined by coordinates, and $A, B, C \ldots$ are parameters.

Expression of a wave surface by the polynomial f will be examined; that is, optimum parameters $(A, B, C, \ldots)$ are calculated.

From the Hartmann's measuring principle, $$\frac{\partial W(X\prime, Y\prime)}{\partial X\prime} = \frac{dx(X\prime, Y\prime)}{l} \quad (4)$$

$$\frac{\partial W(X\prime, Y\prime)}{\partial Y\prime} = \frac{dy(X\prime, Y\prime)}{l}$$

Practically, data represents an inclinations and hence the derivative of each wave surface is used for calculation. In the present invention, measured data represents the inclination of light rays. The inclination can be determined by directly differentiating the wave surface at the coordinates of a position.

The wavefront sensor measures a lateral residual from a reference.

It is known that the following relation holds good in FIG. 7, in which l is the distance between the first converting device 1300 and the first light receiving device 1400. Values $dx(X, Y)$ and $dy(X, Y)$ are calculated for each element of the first converting device 1300, having a center point at X, Y, in which dx and dy are distances along the x-axis and the y-axis between a predetermined origin on the first light receiving device 1400, and a point on the first light receiving device 1400 where the light beam falls on the first light receiving device 1400.

An origin corresponding to one element of the first converting device 1300 is a point on the first light receiving device 1400 where the converted light rays can be measured when the wave surface is uniformly flat, i.e., both the spherical component and the astigmatism component representing the refractive characteristic of the eye are 0 diopter, and there is no residual of irregular astigmatism.

Suppose that dx and dy are deviations of the light beam from the reference point. Then, $$dx(X_i, Y_j) = x_{ij} - x^0_{ij} \quad (5)$$

$$dy(X_i, Y_j) = y_{ij} - y^0_{ij} \quad (6)$$

An expression, (number of measured data)×2, can be obtained by substituting the polynomial f into the expressions (5), (6), and necessary parameters can be obtained by method of least squares.

Although the constant term of f can not be determined because an expression obtained by the derivative of the polynomial f is used, the determination of necessary parameters is sufficient for the present invention.

Concretely, the Zernike's polynomial, i.e., an orthogonal function properly representing aberration in terms of geometrical optics, may be used.

The general term of the Zernike's polynomial is expressed by:

$$Z_\infty(r, \theta) = R^{\infty Loe}(r)\left\{\frac{\sin}{\cos}\right\}(n - 2m)\theta \quad (7)$$

SIN FOR $n - 2m > 0$

COS FOR $n - 2m \leq 0$ $$\therefore R^{\infty Loe}(r) = \sum_{s=1}^{\infty}(-1)^s \frac{(n-s)!}{s!(m-s)!(n-m-s)!}r^{n-2s}$$

More specifically, the Zernike's polynomial is expressed by the following expressions.

$$Z_{00} = 1$$

$$Z_{10} = x$$

$$Z_{11} = y$$

$$Z_{20} = 2xy$$

$$Z_{21} = -1 + 2y^2 + 2x^2$$

$$Z_{22} = y^2 - x^2$$

$$Z_{30} = 3xy^2 - x^3$$

$$Z_{31} = -2x + 3xy^2 + 3x^3$$

$$Z_{32} = -2y + 3y^3 + 3x^2 y$$

-continued $$Z_{33} = y^3 - 3x^2 y$$

$$Z_{40} = 4y^3 x + 4x^3 y$$

$$Z_{41} = -6xy + 8y^3 x + 8x^3 y$$

$$Z_{42} = 1 - 6y^2 - 6x^2 + 6y^4 + 12x^2 y^2 + 6x^4$$

$$Z_{43} = -3y^2 + 3x^2 + 4y^4 - 4x^4$$

$$Z_{44} = y^4 - 6x^2 y^2 + x^4$$

Seventeen sample points (at least sixteen sample points on four rows along the X-axis and four columns along the Y-axis, and one sample point) or above are necessary when those expressions are combined by fourth degree.

Figure 8:
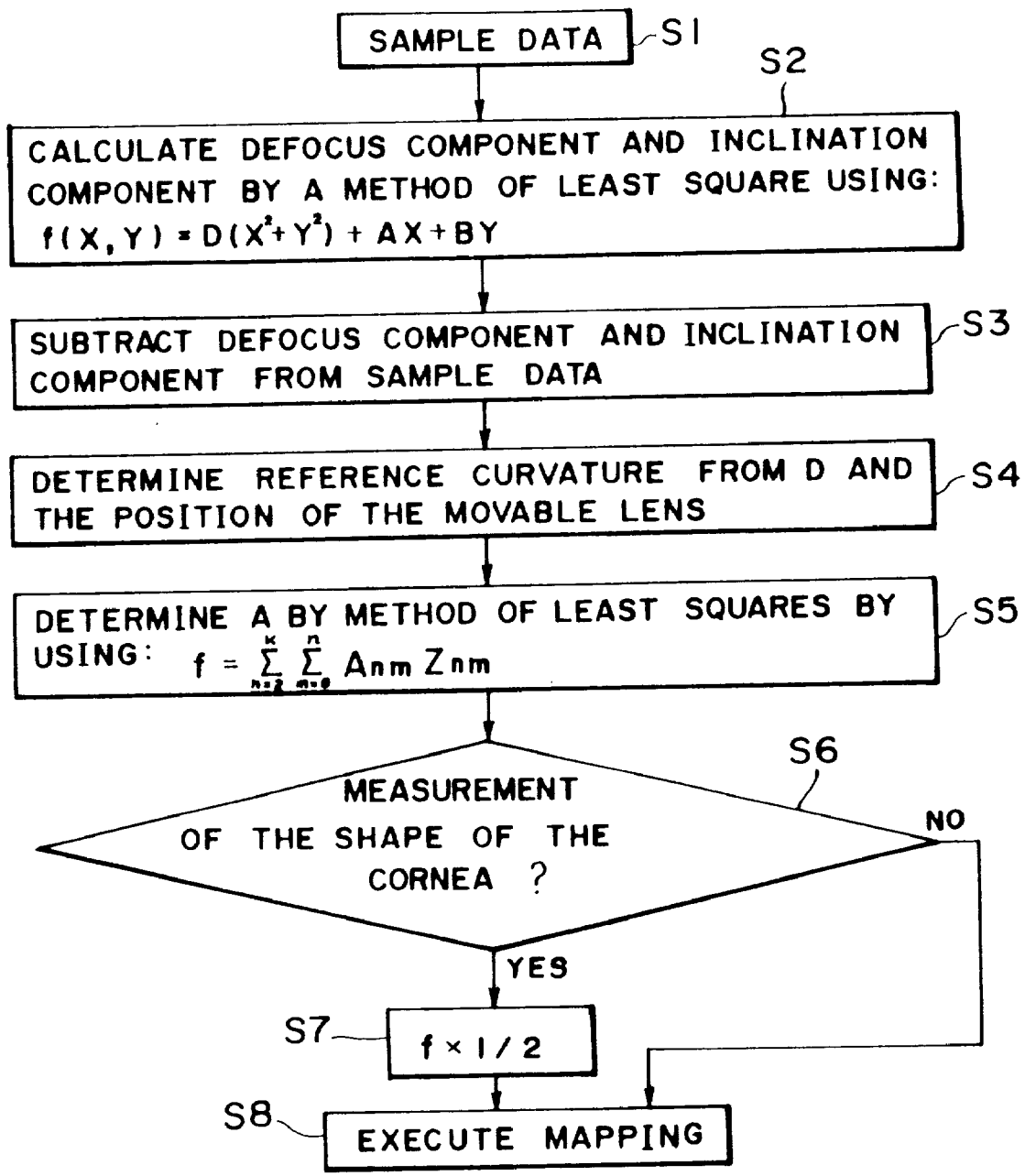
FIG. 8 is a flow chart of assistance in explaining the principle.

Algorithm will be concretely described with reference to FIG. 8.

In step S1, sample data is produced on the basis of the data provided by the first light receiving device 1400. A defocus component and an inclination component are determined by method of least squares in step S2. The defocus component and the inclination component are subtracted from the sample data in step S3. In step S4, a reference curvature is determined on the basis of D and the position of the movable lens. In step S5, A is determined by method of least squares. In step S6, a query is made to see if the shape of the cornea is being measured. If the response in step S6 is affirmative, the value of f is multiplied by ½ in step S7 because the light rays are reflected twice, and mapping is executed in step S8.

If the response in step S6 is negative, step S7 is skipped and step S8 is executed.

[Calculation Using Placido's Disc]

Figure 9:
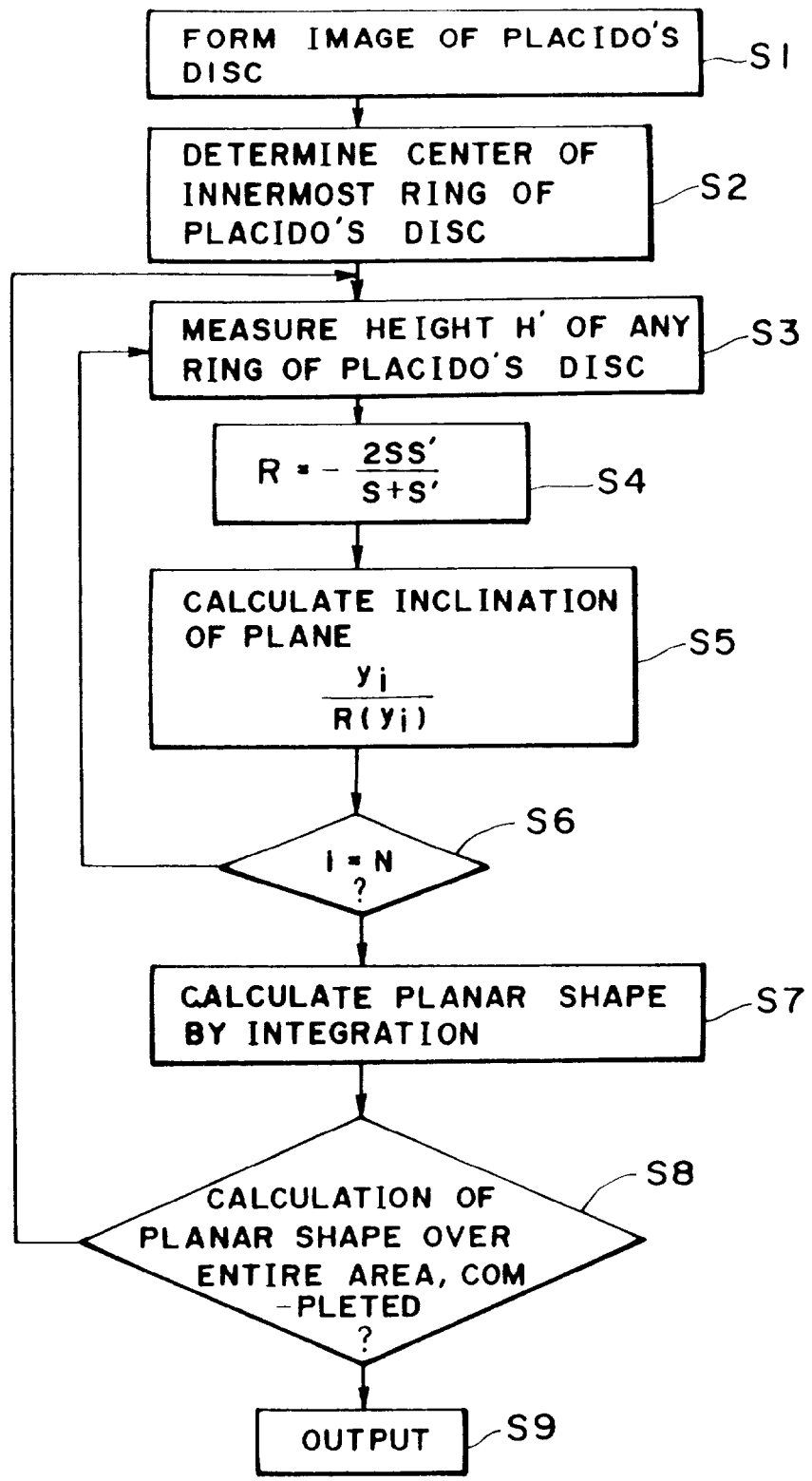
FIG. 9 is a flow chart illustrating steps of measuring a planar shape using the Placido's disc.

The calculation of a planer shape of the cornea of an eye to be examined using the Placido's disc will be described with reference to FIG. 9.

At step S1, the second light receiving optical system 2200 creates an image of the Placido s disc on the basis of the light rays reflected from the cornea 1010 of an eye to be examined. At step S2, the center of the innermost ring of the Placido's disc is determined.

Figure 10:
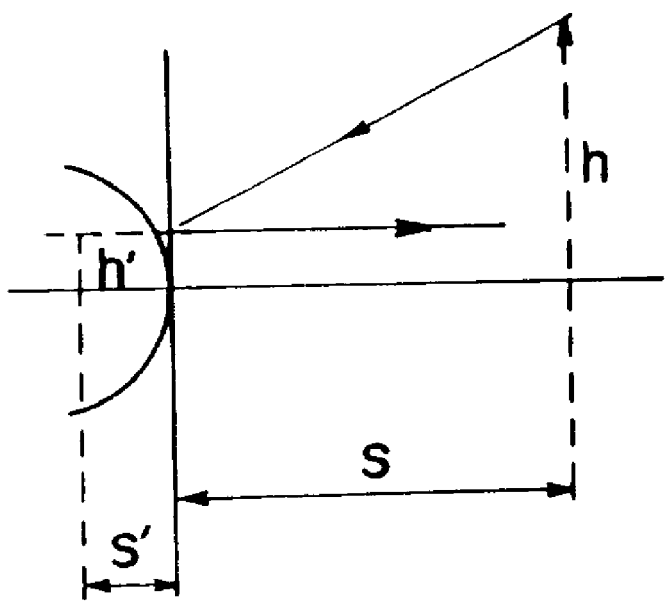
FIG. 10 is a diagram illustrating the principle of measurement using the Placido's disc.

At step S3, a height h' of any one of the rings of the Placido's disc is measured. Referring to FIG. 10, a geometrical relationship between the height h' and a height h of an image of the above ring having the height h' is given by $$(h'/h)=(S'/S)=m$$

where m is a magnification; S' is a distance between the vertex of the cornea and the Placido's disc 2120; and S is a distance between the vertex of the cornea and the image of the Placido's disc.

Here, the values m, S, and S' satisfy the following relationships with R (radius of curvature):

$$m=-(R/2S), \text{ and}$$

$$(1/S)+(1/S')=-(2/R)$$

Consequently, the radius of curvature (R) is expressed by $$R=-2(SS'/(S+S'))$$

At step S4, the radius of curvature (R) is calculated on the basis of the above relationship with S and S'.

At step S5, yi/R(i) is calculated to obtain an inclination of the plane, where i is an integer selected from 1, 2, . . . N. In the first embodiment, for example, N is set at 10. It should be noted that N/2 is equivalent to the number of rings of the Placido's disc.

At step S6, it is judged whether or not yi/R(i) is calculated for all of the numbers from 1 to N, and if not calculated up to N, the process is returned to step S3 at which the calculation is performed again. If it is judged that yi/R(i) is calculated up to N (N=10 in the first embodiment), the process goes on to step S7 at which the inclination factor (yi/R(i)) calculated at step S5 is integrated to obtain the planar shape of the cornea. At step S8, the calculation of the planar shape is performed over the area. If the entire calculation is completed, the process goes on to step S9 at which the results are outputted.

[Concrete Calculation]

The concrete measurement method using an ophthalmologic characteristic measuring apparatus according to the first embodiment will be described below.

Figure 11:
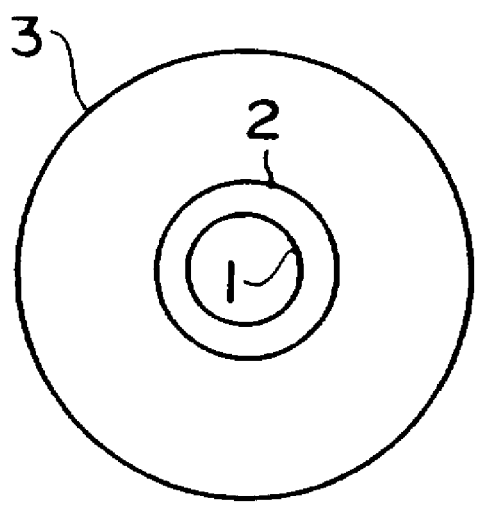
FIG. 11 is a view illustrating measurement regions.

First, as shown in FIG. 11, a measurement range of an eye to be examined is expressed by circles having an innermost circle 1, an intermediate circle 2, and an outermost circle 3. In the first embodiment, the diameter of the circle 1 is 2.9 mm; the diameter of the circle 2 is 3.0 mm; and the diameter of the circle 3 is 9.0 mm.

In the first embodiment, the inside of the circle 2 (first illumination region) is measured and calculated by the first light receiving optical system 1200 using the first converting member 1300, and a region between the outside of the circle 1 and the inside of the circle 3 (second illumination region) is measured arid calculated by the second light receiving optical system 2200 using the Placido's disc 2120. Accordingly, the region between the outside of the circle 1 and the inside of the circle 2 are doubly measured and calculated.

That is to say, in the first embodiment, the first illumination region in the vicinity 1010 of the cornea of the eye to be examined, from which region the first illuminating light rays are reflected and received by the first light receiving optical system 1200, is adjacent or overlapped to the second illumination region in the vicinity 1010 of the cornea of the eye, from which region the second illuminating light rays are reflected and received by the second illuminating optical system 2200.

Second Embodiment

An ophthalmologic characteristic measuring apparatus 20000 according to a second embodiment of the present invention, measures and calculates the shape of the cornea of an eye to be examined in the same manner as that of the first embodiment. That is to say, even in the second embodiment, the inside of the circle 2 is measured and calculated by a first light receiving optical system 1200 using a first converting member 1300, and the region between the outside of the circle 1 and the inside of the circle 3 by a second light receiving optical system 2200 using the Placido's disc 2120. In addition to the above measurement and calculation, the apparatus 20000 of the second embodiment measures a refractive characteristic by a new optical system.

Figure 12:
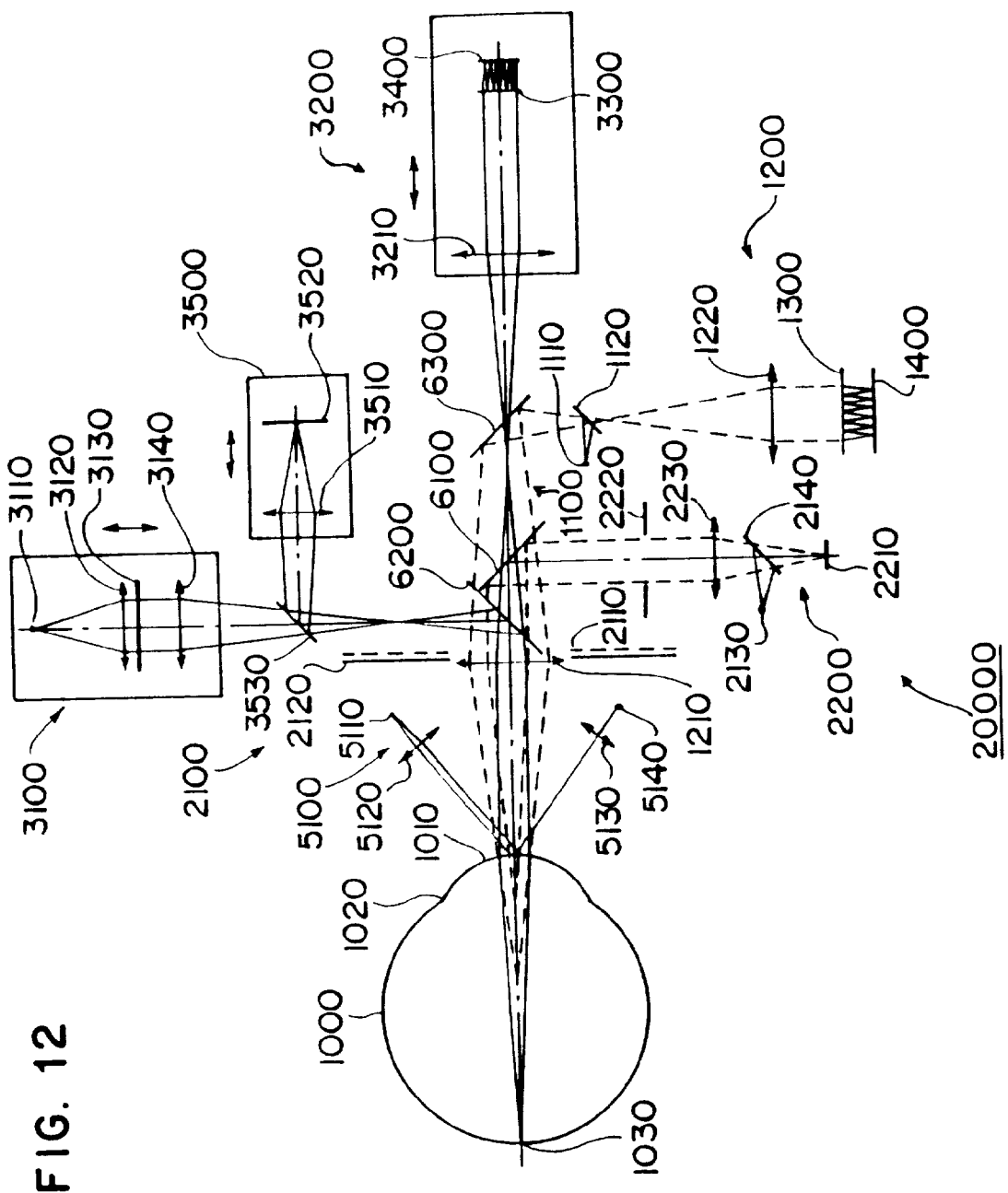
FIG. 12 is a diagram showing the configuration of an ophthalmologic characteristic measuring apparatus according to a second embodiment.

The ophthalmologic characteristic measuring apparatus 20000 according to the second embodiment includes, as shown in FIG. 12, a first light source 1110 for emitting light rays having a first wavelength; a first illuminating optical system 1100 for convergently illuminating a portion near the center of the cornea of an eye to be examined with first illuminating light rays emitted from the first light source 1110; a first light receiving optical system 1200 for receiving the first illuminating light rays reflected from the cornea of the eye and guiding the reflected light rays to a first light receiving unit 1400; a first converting member 1300 for converting the reflected light rays into at least seventeen beams; the first light receiving unit 1400 for receiving a plurality of light rays converted by the first converting members 1300; a second light source 2110 for emitting light rays having a second wavelength; a second illuminating optical system 2100 for projecting an index having a specific pattern on the cornea of the eye with second illuminating light rays emitted from the second light source 2110; a second light receiving optical system 2200 for receiving the second illuminating light rays reflected from the cornea of the eye and guiding the reflected light rays to a second light receiving unit 2210; the second light receiving unit 2210 for receiving the second illuminating light rays from the second light receiving optical system 2200; a third light source 3110 for emitting light rays having a third wavelength different from the first and second wavelengths; a third illuminating optical system 3100 for illuminating a minute region on the retina of the eye with light rays emitted from the third light source 3110; a third light receiving optical system 3200 for receiving light rays reflected back from the retina of the eye and guiding the reflected light rays to a third light receiving unit 3400; a second converting member 3300 for converting the reflected light rays into at least seventeen beams; the third light receiving unit 3400 for receiving a plurality of light rays converted by the second converting member 3300; and an arithmetic unit 9100 for determining the shape of the cornea near the center of the eye on the basis of an inclination angle of the light rays obtained by the first receiving unit 1400; determining the shape of the cornea at the peripheral portion of the eye on the basis of a position of the second light receiving unit 2210, at which position the second light receiving unit 2210 receives the second illuminating light rays; and determining optical characteristic of the eye on the basis of an inclination angle of the light rays obtained by the third light receiving unit 3400.

The first illuminating optical system 1100, first light receiving optical system 1200, second illuminating optical system 2100, and second light receiving optical system 2200 in the second embodiment are the same as those in the first embodiment, and therefore, the explanation thereof is omitted. Here, only the third illuminating optical system 3100 and third light receiving optical system 3200 will be described.

The third illuminating optical system 3100 illuminates a minute region on the retina of an eye to be examined with light rays, having the third wavelength different from the first and second wavelengths, emitted from the third light source 3110.

The third illuminating optical system 3100 includes a first condenser lens 3120, a light screening member 3130, a second condenser lens 3140, and a second dichroic mirror 6200.

The third illuminating optical system 3100 can be moved along its optical axis depending on the refractive power of the eye to focus light rays on the eyeground of the eye. The third illuminating optical system 3100 of the second embodiment can be moved along its optical axis in a distance range corresponding to a range of about −25 diopter to about +25 diopter.

It may be desirable that the third light source 3110 is capable of emitting light having a high spatial coherence and a low temporal coherence. The third light source 3110 of the second embodiment is a SLD, which is a point light source having a high luminance.

The third wavelength of the third light source 3110 of the second embodiment may be a wavelength in the infrared range, for example, 840 nm.

The light screening member 3130 creates an illuminating state 1A in which the eye is illuminated through a portion near the periphery of the pupil, and an illuminating state 1B in which the eye is illuminated through a portion near the center of the pupil.

The light screening member 3130 can be composed of a variable diaphragm including a first diaphragm (for illuminating state 1B) having an aperture in its center portion, and a second diaphragm (for illuminating state 1A) having an aperture in its peripheral portion.

The measurement of the refractive characteristic may be performed for a screened portion at that time by the third illuminating optical system 3100. This prevents the measurement from being affected by reflection from the cornea.

When the first diaphragm of the variable diaphragm is inserted in the optical path, a region screened by the central screening portion is measured. When the second diaphragm of the variable diaphragm is inserted in the optical path, a region corresponding to a portion around the central aperture is measured.

The light screening member 3130 may be a liquid crystal device capable of forming an aperture in its central portion to set the illuminating state 1A and of forming an aperture in its peripheral portion to set the illuminating state 1B.

Accordingly, the light screening member 3130 of the third illuminating optical system 3100 is at a point substantially conjugate with the pupil of the eye, and is capable of creating the first illuminating state 1A for illumination through a region near the center of the pupil of the eye and the second illuminating state 1B for illumination through a portion near the periphery of the pupil of the eye.

The third light receiving optical system 3200 receives light rays reflected back from the retina of the eye and guides the reflected light rays to the light receiving unit. The third light receiving optical system 3200 includes a relay lens 3210 and the second converting member 3300 for converting the reflected light rays into at least seventeen beams.

The third illuminating optical system 3100 and the third light receiving optical system 3200 are moved in an interlocking manner while keeping a relationship to maximize a signal peak obtained at the third light receiving unit 3400 on the basis of the light rays which have been convergently illuminated by the illuminating optical system 3100 and reflected back to the third light receiving optical system 3200. That is to s,ay, the third illuminating optical system 3100 and the third light receiving optical system 3200 are moved in directions to increase the peak of the output signal of the third light receiving unit 3400 and are stopped at positions where the intensity of the light rays falling on the third light receiving unit 3400 is maximized. Consequently, light rays emitted from the third light source 3110 are focused on the retina.

The second converting member 3300 of the third light receiving optical system 3200 is conjugate with the light screening member 3130 of the third illuminating optical system 3100. The second converting member 3300 and the light screening member 3130 are conjugate with an iris 1020.

The third light receiving optical system 3200 is movable along the optical axis depending on the refractive power of the eye to be examined. The third light receiving unit 3400 or the second converting member 3300 is substantially conjugate with the cornea 1010.

As shown in FIG. 2, the arithmetic unit 9100 is connected to a control unit 9200, and it carries out calculation of optical characteristics or the like on the basis of a command given by the control unit 9200.

The control unit 9200 controls the entire apparatus including the arithmetic unit 9100. An alignment processing unit 9300 controls alignment processing.

A display unit 9400 displays data provided by the arithmetic unit 9100. The display unit 9400 is capable of displaying optical characteristics of the eye and the shape of the cornea of the eye calculated by the arithmetic unit 9100.

The arithmetic unit 9100 of the present invention estimates optical characteristics of the eye from the shape of the cornea, and compares the estimated optical characteristics with optical characteristics determined on the basis of the output of the third light receiving unit 3400, to thereby find abnormal optical characteristics due to a factor other than the shape of the cornea. The optical characteristics can be calculated by a ray tracing method or a simpler approximation method. The position of a secondary point light source on the retina may be a model value from the S value of refractive characteristic measurement at that time.

Figure 13:
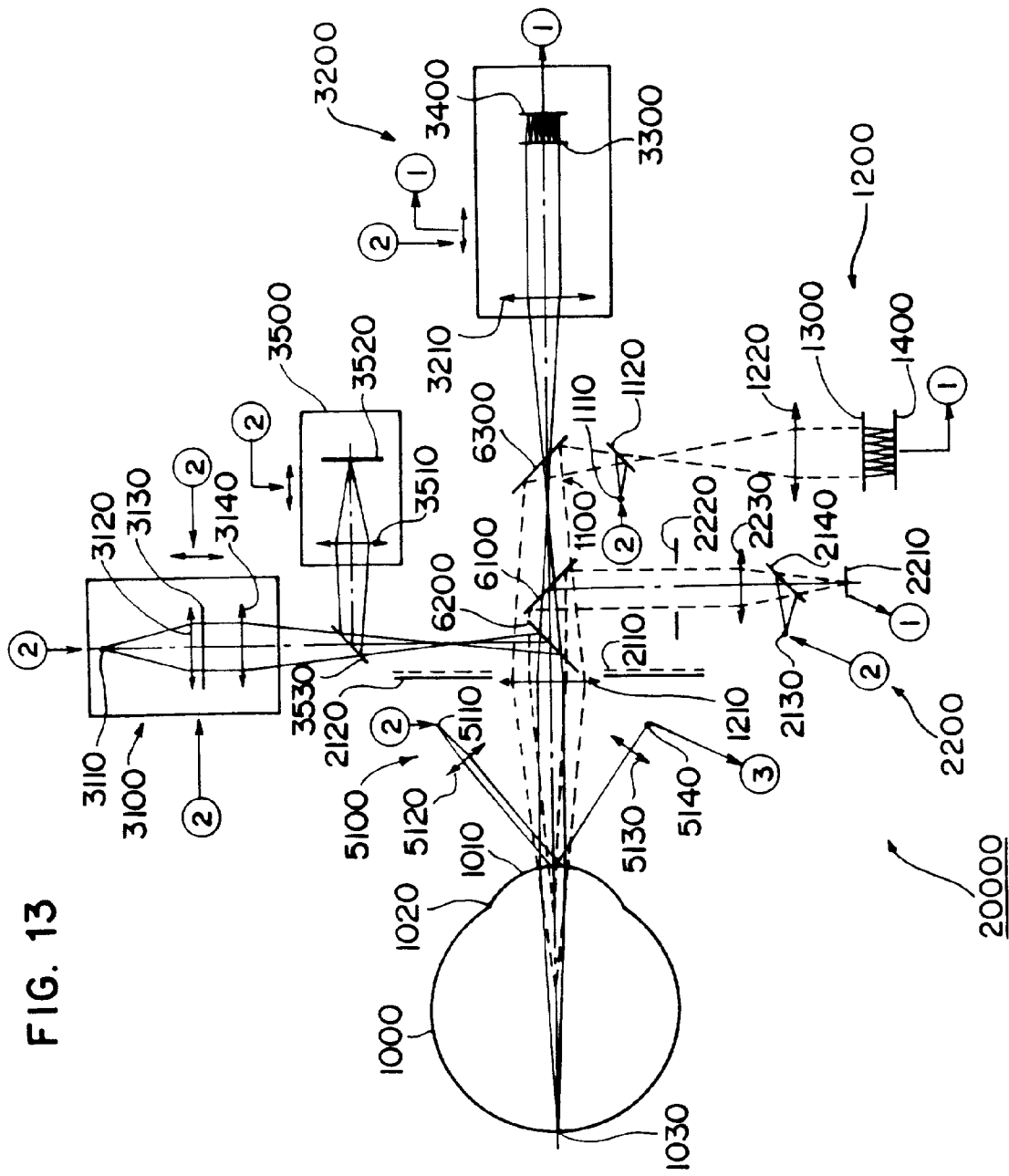
FIG. 13 is a diagram showing the electric configuration of the ophthalmologic characteristic measuring apparatus according to the second embodiment.

FIG. 13 illustrates the connection of the components of the ophthalmologic characteristic measuring apparatus with electric components.

A fixation point optical system 3500 is composed of a fixation point focusing lens 3510 and a fixation point 3520.

Light rays from the third illuminating optical system 3100 and light rays from the fixation point optical system 3500 are rendered coaxial with each other by means of a third dichroic mirror 3530.

The fixation point optical system 3500 can be adjusted to show a pattern to the eye, to blur an image or to fix the line of sight of the eye. The fixation point optical system 3500 is movable along its optical axis according to the refractive power of the eye.

A third dichroic mirror is inserted, between the first illuminating optical system 1100 and the first light receiving optical system 1200 in the second embodiment, for 90° deflection of light therebetween.

The other composing elements, functions, and operations of this embodiment are the same as those of the first embodiment, and therefore, the explanation thereof is omitted.

As described above, the ophthalmologic characteristic measuring apparatus of the present invention having the above configuration includes: a first light source for emitting light rays having a first wavelength; a first illuminating optical system for illuminating convergently a portion near the center of curvature of the cornea of an eye to be examined with first illuminating light rays emitted from the first light source; a first receiving optical system for receiving the first illuminating light rays reflected back from the cornea of the eye; a first converting member for converting the reflected light rays into at least seventeen beams; a first light receiving unit for receiving a plurality of light beams converted by the first converting member; a second light source for emitting light rays having a second wavelength; a second illuminating optical system for projecting an index having a specific pattern on the cornea of the eye with second illuminating light rays emitted from the second light source; a second light receiving optical system for receiving light rays reflected back from the cornea of the eye; a second light receiving unit for receiving the second illuminating light rays from the second light receiving optical system; and an arithmetic unit for determining the shape of the cornea near the center of the eye on the basis of an inclination angle of the light rays obtained by the first light receiving unit and determining the shape of the cornea at the periphery of the eye on the basis of a position of the second light receiving unit, at which position the second light receiving unit receives the second illuminating light rays, and accordingly, the apparatus of the present invention exhibits a desirable effect capable of reducing the size of the objective side, thereby making compact the overall size of the apparatus.

What is claimed is:

1. An ophthalmologic characteristic measuring apparatus comprising:

a first light source for emitting light rays having a first wavelength;

a first illuminating optical system for illuminating convergently a portion near the center of curvature of the cornea of an eye to be examined with first illuminating light rays emitted from said first light source;

a first receiving optical system for receiving the first illuminating light rays reflected back from the cornea of the eye;

a first converting member for converting the reflected light rays into at least seventeen beams;

a first light receiving unit for receiving a plurality of light beams converted by said first converting member;

a second light source for emitting light rays having a second wavelength;

a second illuminating optical system for projecting an index having a specific pattern on the cornea of the eye with second illuminating light rays emitted from said second light source;

a second light receiving optical system for receiving light rays reflected back from the cornea of the eye;

a second light receiving unit for receiving the second illuminating light rays from said second light receiving optical system; and an arithmetic unit for determining the shape of the cornea near the center of the eye on the basis of an inclination angle of the light rays obtained by said first light receiving unit and determining the shape of the cornea at the periphery of the eye on the basis of a position of said second light receiving unit, at which position said second light receiving unit receives the second illuminating light rays.

2. An ophthalmologic characteristic measuring apparatus according to claim 1, wherein said second illuminating optical system is configured to project a Placido's disc composed of a plurality of concentric rings as said index having the specific pattern, and said second light receiving optical system includes an objective lens with a telecentric diaphragm arranged at a focal point of said objective lens on the objective side.

3. An ophthalmologic characteristic measuring apparatus according to claim 1 or 2, wherein a first illumination region in the vicinity of the cornea of the eye, from which region the first illuminating light rays are reflected and received by said first light receiving optical system is adjacent or overlapped to a second illumination region in the vicinity of the cornea of the eye, from which region the second illuminating light rays are reflected and received by said second light receiving optical system.

4. An ophthalmologic characteristic measuring apparatus according to any one of claims 1 to 3, further comprising:

a third light source for emitting light rays having a third wavelength different from the first and second wavelengths;

a third illuminating optical system for illuminating a minute region on the retina of the eye with light rays emitted from said third light source;

a third light receiving optical system for receiving light rays reflected back from the retina of the eye;

a second converting member for converting the reflected light rays into at least seventeen beams; and a third light receiving unit for receiving a plurality of light rays converted by said second converting members;

wherein said arithmetic unit determines optical characteristics of the eye on the basis of an inclination angle of the light rays obtained by said third light receiving unit.

* * * * *